(12) United States Patent
Weinberg et al.

(10) Patent No.: US 6,699,433 B2
(45) Date of Patent: Mar. 2, 2004

(54) METHOD OF DECONTAMINATION OF WHOLE STRUCTURES AND ARTICLES CONTAMINATED BY PATHOGENIC SPORES

(76) Inventors: Mark J. Weinberg, 1609 SW. 15th Ter., Fort Lauderdale, FL (US) 33312; Rudolf H. Scheffrahn, 1330 NW. 99th Ave., Plantation, FL (US) 33322

( * ) Notice: Subject to any disclaimer, the term of this patent is extended or adjusted under 35 U.S.C. 154(b) by 140 days.

(21) Appl. No.: 10/109,195

(22) Filed: Mar. 28, 2002

(65) Prior Publication Data

US 2003/0129082 A1 Jul. 10, 2003

Related U.S. Application Data

(60) Provisional application No. 60/346,282, filed on Jan. 9, 2002.

(51) Int. Cl.[7] ................................. A61L 2/20
(52) U.S. Cl. ........................... 422/32; 422/4
(58) Field of Search ....................... 422/4, 32

(56) References Cited

U.S. PATENT DOCUMENTS 6,588,140 B1 * 7/2003 Johnson et al. ............... 43/124

* cited by examiner

Primary Examiner—Hoa Van Le
(74) Attorney, Agent, or Firm—Malin, Haley & DiMaggio, P.A.

(57) ABSTRACT

The present invention is a method of decontaminating a structure contaminated by pathogenic microorganisms such as *Bacillus anthracis* and its spores, *B. subtilis* var *niger* and its spores, and *B. stearothermophilus* and its spores, comprising the steps of sealing a contaminated structure sufficiently to enable retention of a gas, introducing methyl bromide gas into sealed contaminated structure to a concentration of methyl bromide in an amount sufficient to deactivate said pathogenic microorganisms and disable germination of pathogenic bacteria spores, and maintaining said sealed contaminated structure with said concentration of methyl bromide at a sufficient temperature for a sufficient period of time, and deactivating said pathogenic microorganisms and disabling germination of said pathogenic bacteria spores associated with said contaminated structure. The method is performed approximately in the range of 20° C. to 40° C., and the concentration of methyl bromide is about 200 mg/l to 303 mg/l during the decontamination. High humidity levels are preferred.

27 Claims, 1 Drawing Sheet

METHOD OF DECONTAMINATION OF WHOLE STRUCTURES AND ARTICLES CONTAMINATED BY PATHOGENIC SPORES

This patent application claims priority to and the benefit of U.S. patent application Ser. No. 60/346,282 filed on Jan. 9, 2002.

BACKGROUND OF THE INVENTION

1. Field of Invention

The instant invention relates to a novel method and means for the efficient, safe, and economic decontamination of entire physical structures, such as buildings, and/or articles contaminated by microorganisms inclusive of pathogenic spores.

2. Prior Art

The prior art of eradication of entire buildings of insects such as termites, cockroaches, wood-boring beetles, rats, mice, bats and other such arthropod and vertebrate animals has, over the last approximately sixty years, consisted of covering and sealing the structure to be treated with a vinyl tarpaulin and, thereafter, introducing the selected fumigant into the structure covered by or confined within the tarpaulin. Among the various fumigants used in the prior art for this purpose has been methyl bromide, a USEPA registered pesticide. However, due to the ozone-depleting properties of methyl bromide as have been recognized by the Montreal Protocol of 1992, methyl bromide was officially added to the list of ozone-depleting chemicals and, pursuant thereto, its production was frozen at 1991 levels thereof. Further, any chemical with an ozone depletion potential (ODP) of greater than 0.02 was, under the Protocol, banned at the end of 2000 and, in the case of methyl bromide, its use in the United States has been banned by the Environmental Protection Agency ("EPA") effective in 2005. Moreover, neither methyl bromide nor other known structural fumigants, have ever been employed for the purpose of decontamination of a structure which are contaminated by microorganisms that are pathogenic to humans including bacteria (prokaryota).

Methyl bromide has been used as a fumigant since the 1930s to control pests in soil, stored commodities, structures and shipments that must meet agricultural quarantine regulations. The major use in agriculture is soil fumigation. It is an extremely effective herbicide, nematicide, insecticide, and fungicide. It is important for the large-scale commercial production of strawberries, tomatoes, peppers, melons, grapes, cucumbers, eggplants, ornamentals, and tobacco. In addition, U.S. regulations require that a wide array of imported food and non-food commodities be fumigated with methyl bromide as a condition of entry into the country. Methyl bromide has never been employed as a means for decontamination of structures of human pathogens such as viruses and hazardous bacteria. Rather, if the contamination of a structure was known to be limited to a particular surface or article, one could employ bleach (sodium hypochlorite), a foam, such as Sandia foam, or a toxic gas, such as chlorine dioxide, which are commonly unstable and/or explosive.

Methyl bromide ($CH_3Br$, also abbreviated as MeBr), a member of the chemical family of alkyl halides, is a colorless and non-flammable gas, which has no odor at toxic levels. It is stable under normal conditions of handling and use. Methyl bromide gas is commercially available at a purity greater than 99% from Great Lakes Chemical Corporation (West Lafayette, Ind.) under the trade name Meth-O-Gas® 100 and Meth-O-Gas® Q. Most fumigation treatments are recommended on the basis of dosage for a certain volume, expressed in pounds per 1000 cubic feet (lb/1000 $ft^3$) in the industry, and in milligram per liter (mg/l) using the metric system. The common dosages used for treating commodities range from 1 lb/1000 $ft^3$ for dried fruits such as dried apples and prunes, to 8 lb/1000 $ft^3$ for cotton seeds, equivalent of from 16 to 128 mg/l. For structural fumigations, such as in termite infested houses and buildings, the common dosage is from 1 to 3 lb/1000 $ft^3$, equivalent of from 16 to 48 mg/l. An important factor used in the industry is the amount of gas acting on the pests over a certain period of time, expressed as the product of concentration and time (CT product, mg-hr/l). The use of methyl bromide has never been considered at the concentration, temperature, and time combinations suggested herein.

Given the new reality of bio-terrorism and its potential in the wake of the events of September, 2001, much concern and attention have been directed to the decontamination of entire buildings that have been the subject of a biological attack such as occurred in Florida, Washington, D.C., and various U.S. Post Offices in New York, New Jersey, Connecticut and elsewhere. Government, inclusive of the EPA and CDC, as well as research community and industry have lacked experiences other than that of decontaminating buildings subjected to a purely chemical contamination, such as by asbestos or PCBs and therein has had no experience with the many problems related to the decontamination of entire buildings, parts of which have been infected (or potentially infected) by a bio-weapon consisting of a microorganism such as a virus, bacteria or spores thereof. Historically, structural decontaminations of biological weapons occurred at an Army facility at Ford Detrick in 1970 and 1971 for a building previously used for producing *Bacillus anthracis*, commonly known as anthrax. The building was decontaminated twice using formaldehyde gas, and further hydrochloric acid was forced through pipes and valves that carried a bacteria mixture. Anthrax spores and other bacteria were not found after the decontamination. However, the damage by the caustic decontamination has threatened the structural integrity of the building. In light thereof, the EPA and CDC, after consultation with scientists, public health specialists, industry experts and even historians on the subject of bio-weapons, settled on the use of chlorine dioxide gas on a massive scale, never before attempted, as a means of decontaminating buildings exposed to a bio-weapon and, particularly, spores of anthrax. As such, operating with little historical or scientific precedent, EPA/CDC have attempted to employ, in substantial quantity, chlorine dioxide gas which, in the past, had been employed only in context of purification of drinking water. In these efforts, the EPA determined that use of chlorine dioxide gas on a large scale entails several hazards and problems, this apart from an underlying question with regard to the concentration, temperature, humidity and time of exposure necessary to kill anthrax spores in sufficient quantity. For example, the humidity within a building to be so decontaminated must be first be elevated from an ambient level of about thirty percent to that of seventy percent, which is considered the optimum level for chlorine gas to kill spores of anthrax. Furthermore, because of the extreme oxidative properties of chlorine dioxide, substantially all equipment and furniture, within a building to be decontaminated must be removed to preclude corrosion or degradation of the surfaces thereof by the oxidative effect of the chlorine dioxide. Further, a special chemical, such as sodium bisulfate, must be employed to neutralize and vent the chlorine dioxide from the building itself. Then, all removed equipment and furniture must be brought back into the building after being fumigated in chambers with flammable ethylene oxide gas. Thereafter, test strips containing a bacterial endospore (*Bacillus subtilis* var. *niger*) more chemically resistant than anthrax spores are used to verify the effectiveness of the chlorine dioxide decontamination.

In view of the above, an urgent need has arisen for a method of decontamination of whole buildings (including the inside, outside, duct work and piping therein,) that will not only obviate the need to remove sensitive articles such as photographs, documents, and computers, and heavy items such as furniture, but which will also obviate the need to pump steam into the structure to elevate the humidity thereof and that does not require a special chemical to neutralize the active agent beyond these issues is a need for a method that can provide a higher level of confidence that the targeted pathogenic organism has, in fact, been killed, and therefore is unable to germinate.

In spore-forming bacteria, the spore is protected from environmental extremes of drought and temperature by a coat made of numerous cross-linked proteins (Driks, A. 1999. *Bacillus subtillis* spore coat. Microbiol Molec. Biol. Rev. 63:1–20). It has been determined that spore coats or shells exhibit a considerable degree of uniformity in their chemical linkages, such that the shell of one spore is substantially similar in chemical structure to the shell of other spores and, in particular, spores of Bacillus which is the genus of a species of bacteria, namely, *B. subtilis* var *niger*, employed as the test bacteria upon test strips, that has become a universally accepted standard for determination of whether a bacterial spore has been killed by a treating agent or method. These spores and bacteria are also used to test the efficacy of treatments for killing *B. anthracis*.

The instant invention therefore addresses the need for a more reliable, comprehensive, convenient, and cost-effective method of decontamination of entire structures and their contents that have been contaminated, or potentially contaminated with pathogenic microbes including, without limitation, anthrax and spores thereof.

SUMMARY OF THE INVENTION

The present invention comprises methods of using methyl bromide as an anti-microbial agent in the decontamination of whole structures or articles that have been contaminated, or may be contaminated, with microorganisms such as bacterial spores. This invention is based on a new use of methyl bromide, a non-flammable, non-corrosive, and E.P.A. registered pesticide. The instant method entails the gas-tight sealing of the entire building to be decontaminated under tarpaulins or other equivalent means. After the building is sealed, a sufficient amount of methyl bromide gas is introduced within the seal so that methyl bromide diffuses into all parts of the building, its surfaces and articles therein. The sealed structure is maintained with the concentration of methyl bromide at a sufficient temperature for a sufficient period of time. This process renders pathogenic bacterial spores in or associated with the structure or its contents nonviable so that germination will not occur when the spore is exposed to a favorable environment for germination. The method further comprises a step of unsealing and aerating decontaminated structure to aerate the methyl bromide gas, without requirement for any special purpose cleaning or deactivation agent, either in gaseous form mixed with air, or as a scrubbing procedure following the fumigation.

The application of methyl bromide using the method of the present invention, at temperature greater than 20° C., preferably greater than 25° C., and with a concentration of methyl bromide about 200 mg/l and above, and an exposure time greater than 30 hours, prevents germination of *B. subtilis* var. *niger* and *B. stearothermophilus* spores. In additional field testing, the application of methyl bromide using the method of the present invention, at temperature between 28° C. and 38° C., and with a concentration of methyl bromide about 250 to 350 mg/l, and an exposure time of approximately 48 hours, also prevents germination of these spores. The method of the present invention provides a marked improvement in coverage, level of confidence, and cost-effectiveness of result over existing methods of structural microbial decontamination.

It is accordingly an object of the invention to provide an improved method of whole structure decontamination for pathogenic microbes.

It is another object to provide a method of the above type, which does not require the removal of all contents of a structure to be decontaminated or the elevation of the humidity, therein.

It is a further object of the invention to provide a method of structural decontamination for pathogenic spores without subjecting the interior of a building as so treated to oxidative agents or requiring the use of special cleaning agents to effect removal of the treating agent at the end of the process.

It is a still further object to provide a method of the above type to more cost-effectively, safely and reliably decontaminate a structure of microbial pathogens including, without limitation, *Bacillus anthracis* spores.

It is another object to provide a method of the above type comprising a use of methyl bromide as a decontaminating agent for bacteria and their spores.

It is a still further object of the invention to provide a method of the above type in which the effectiveness thereof may be authoritatively ascertained through the use of test strips containing bacteria of a type more resistant to heat and toxic chemicals than *B. anthracis* and which are universally accepted as a measure of the effectiveness of microbial decontamination.

It is a yet further object to provide a method of the above type employing long established procedures for fumigation of structures for the control of arthropod and vertebrate pest animals, however, only substituting the use of methyl bromide in its inventive parameters of use, in lieu of existing fumigants.

It is yet another object of the invention to use a chemical for decontaminating *B. anthracis* and its spores which is non-flammable and stable.

It is still another object of the invention to provide a method of the above type comprising a use of methyl bromide as a decontaminating agent for bacteria and their spores which generally does not harm electronic equipment or sensitive materials which might be damaged by a strong oxidizing agent It is yet another object of the invention to provide a method of the above type that allows for an unlimited volume for treating areas.

The above and yet other objects and advantages of the present invention will become apparent from the hereinafter set forth Brief Description of the Drawings and Detailed Description of the Invention.

DETAILED DESCRIPTION OF THE INVENTION

Figure 1:
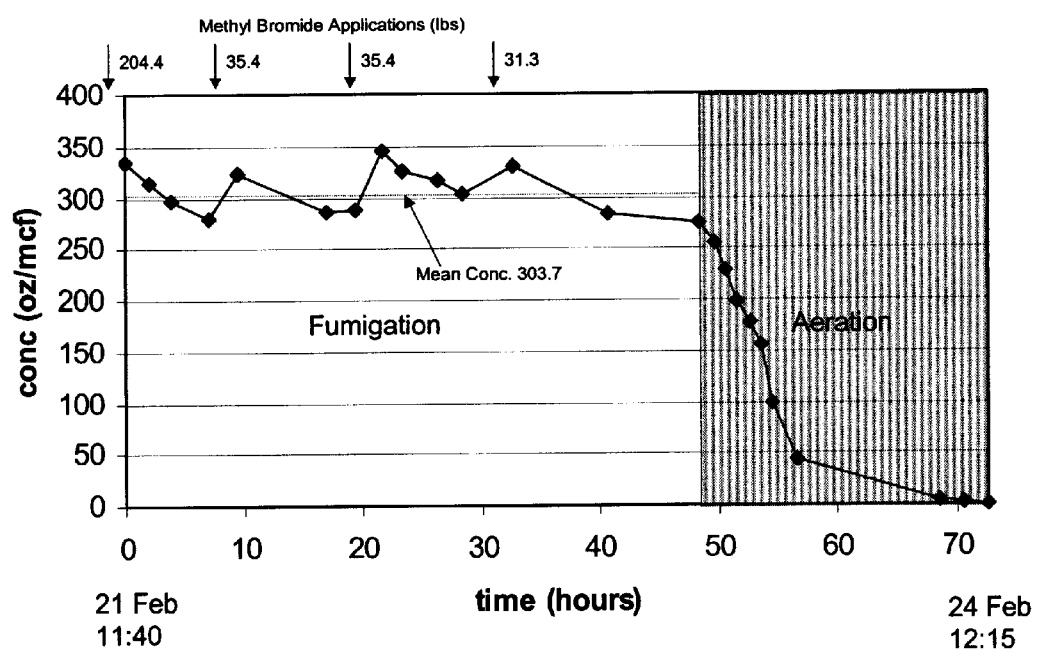
FIG. 1 is a chart detailing the methyl bromide concentration during trailer fumigation and aeration of Example 4.

In one embodiment, the present invention relates to a method of decontaminating a structure contaminated by pathogenic microorganisms. The method comprises the steps of sealing a contaminated structure sufficiently to enable retention of a gas; introducing a methyl bromide gas into the sealed contaminated structure at a concentration of methyl bromide in an amount sufficient to deactivate the pathogenic microorganisms; and maintaining the sealed contaminated structure with the concentration of methyl bromide at a sufficient temperature for a sufficient period of time, resulting in deactivation of the pathogenic microorganisms and prevention of germination of the pathogenic bacteria spores in or associated with the contaminated structure.

For the purpose of the present invention, the term "deactivation" means killing pathogenic bacteria and bacterial spores so that germination will not occur, in another word, disabled, when the spores are exposed to a favorable environment for germination. The term "structure" includes, but not limited to, a room, a residential or a commercial building, a mobile home, a vehicle, a train, a boat, or an airplane.

Preferably, the methyl bromide gas used in the above-described process is a pure gas. A suitable example is a commercial product under the trade name Meth-O-Gas® 100 obtained from Great Lakes Chemical Corporation (West Lafayette, Ind.). The purity of Meth-O-Gas® 100 is greater than 99%, with trace amount of dimethyl ether and methyl chloride.

Furthermore, methyl bromide, as the active agent for deactivating pathogenic microorganism, can also be used together with other additives. Suitable additives include inert carrier gases which do not interference methyl bromide's function, other gaseous chemicals which may further enhance the effect of methyl bromide against the microorganisms, and warning agents. Suitable examples of additives are carbon dioxide and chloropicrin, and both are compatible with methyl bromide. Since methyl bromide is an odorless gas at a toxic concentration, it can be desirable in certain circumstances to introduce a small amount of warning agent into the methyl bromide gas filled structure to alert the risk in case of leaking, or before the structure is ready for reentry after decontamination. Chloropicrin, available commercially, has been used as a warning agent for fumigation because of its pungent odor and being an irritating lachrymator. Additionally, a methyl bromide gas containing a small amount of chloropicrin is also commercially available. One example is the methyl bromide gas containing 2% or 5% of chloropicrin produced by Great Lakes Chemical Corp. under the trade name of Brom-O-Gas®.

Efficacy of the process of decontaminating a structure contaminated by pathogenic microorganisms can be tested by using spore strips. Prior to the start of the fumigation bacterial spore strips containing $10^6$ ((1 million spores per strip) of *B. subtilis* var. *niger* are placed throughout, in and/or associated with, the contaminated structure in order to evaluate the effectiveness of the decontamination process after completion. Similar, if not identical spore strips were used as test markers for monitoring the effectiveness of the chlorine dioxide fumigation that was used in an attempt to decontaminate parts of the Hart Senate Building in December 2001. These strips are also standard indicators for verifying the efficacy of chemical, dry-heat, and steam sterilization equipment that is frequently used in dental and medical facilities. The $10^8$ *Bacillus subtilis* var. *niger* spore strips are derived from ATCC (American Type Culture Collection, the repository where spore crops are obtained) #9372 and can be purchased from Raven Biological Laboratories in Omaha, Nebr. Upon completion of the sterilization or decontamination process, the strips are recovered and sent to a laboratory where they are incubated in a tryptic soy broth for culturing. After a certain period of time, typically 48 hours, a color change of the broth, for example from purple to yellow, indicates spore germination and vegetative growth of the Bacillus. If however, after one week the broth color does not change, then the spores are not viable and the decontamination and/or sterilization process is successful.

It is understood by those skilled in the art that the dosage of a fumigant, and hence its effectiveness, is expressed by the product of the fumigant concentration and the time of exposure, commonly called concentration and time product, abbreviated as CT. The unit of CT is mg-hr/l if expressed in metric system. However, it is found that for the purpose of the present invention CT is not the dominant factor for achieving decontamination of pathogenic microorganisms, particularly bacteria spores. Instead, concentration of the methyl bromide gas and temperature used for the exposure play more critical roles.

Examples 1, 2 and 3 illustrate the functions of temperature and the concentration of methyl bromide under laboratory test conditions. Example 4 illustrates the functions of temperature and the concentration of methyl bromide under field test conditions. As shown in Table 1, at temperature of 19° C. and methyl bromide concentrations from 48 to 80 mg/l (theoretical value), *B. subtilis* spores, after an exposure time as long as 164 hours, still germinated. Therefore, the decontamination was not successful. On the contrary, as shown in Table 2, when the exposure temperature was raised to 27° C., with a methyl bromide concentration of 320 mg/l (theoretical value) *B. subtilis* spore germination was successfully disabled, after exposure under such a condition for 72 hours. Moreover, as shown in Table 3, when the exposure temperature was further raised to 32° C., with a methyl bromide concentration of 240 mg/l (theoretical value) *B. subtilis* spore germination was successfully disabled, after exposure under such a condition for only 38 hours. However, at the same temperature (32° C.) a methyl bromide concentration of 160 mg/l (theoretical value) was not sufficient to stop germination of the spores. In addition, as shown in Table 4, when in a field environment the exposure temperature was put in the range of 28° C. to 38° C., with a methyl bromide concentration of 250 to 350 oz/mcf, germinations of *B. subtilis* and *B. stearo*. at concentrations of $10^6$ and $10^5$, respectively were successfully disabled, after exposure under these conditions for 48 hours. Moreover, germinations of these spores in strips with concentrations of $10^8$, were also successfully disabled after exposure under these conditions for 48 hours.

Furthermore, Example 2 also illustrates the effect of methyl bromide exposure to office commodities commonly present in office buildings. The results showed that with 96 hours exposure at 27° C. to a methyl bromide concentration as high as 320 mg/l, no observable damage had occurred to the office commodities. Unaltered data were recovered from the storage media (video tape, CD, and Zip diskette), the calculator functioned, and the unexposed film was exposed and developed without damage. This demonstrated utility of the method of the present invention for decontaminating whole structures, such as office buildings and common office commodities contained therein.

It is noted methyl bromide concentrations listed in Tables 1–3 were obtained from the theoretical calculation based on syringe-injected volume of the methyl bromide gas. As stated in the examples, upon increasing the temperature and re-equilibrating the chambers to atmospheric pressure, there is an estimated loss of methyl bromide of about 8%.

Furthermore, it is also known that up to 6% of methyl bromide can be absorbed by the structure under the decontamination treatment. Therefore, the airborne concentration of methyl bromide retained in the sealed structure is about 8 to 15% lower than the theoretical value. More specifically, for a theoretical value of 240 mg/l, the actual concentration is between 204 mg/l and 220 mg/l.

Therefore, for the purpose of the present invention it is preferred to carry out the decontamination process at a temperature greater than 20° C., more preferably at a temperature greater than 25° C., and most preferably at a temperature about 27° C. and above. On the other hand, the concentration of methyl bromide used for the decontamination of pathogenic microorganisms is preferably about 200 mg/l and above. In accordance with the data obtained from the field test described in Example 4, additional optimal constraints for temperature, time and concentration of the fumigation are also described below.

In the fumigation industry, the amount of methyl bromide required to achieve a certain target concentration is calculated first. After introducing the calculated amount of methyl bromide into a sealed structure, the actual methyl bromide concentration is measured using gas detectors described hereinafter. During the fumigation, the methyl bromide concentration can be monitored frequently, and can be maintained at the desired level by refill if it is needed.

Since the effective exposure temperatures in the range of greater than 20° C. to about 38° C. can be conveniently achieved in the field, and since introducing methyl bromide gas into a sealed structure has been practiced many years in the fumigation industry, the effective decontamination method demonstrated in the laboratory scale can be implemented conveniently in the field by using the structural fumigation techniques. It is known to those in the fumigation industry, these techniques require that the building exterior be completely covered with tarpaulins that are clamped together at their seams and sealed at ground level with "sand snakes". Some buildings with gas tight outer walls and roof structures can be sealed using polyethylene sheeting taped over ventilation systems, windows, and other locations where gas might diffuse from the building. Once the building is sealed, methyl bromide is added by allowing the pressurized liquid in methyl bromide cylinders to pass through a heat exchanger where the methyl bromide becomes gaseous and from there it is introduced by hose into the building interior. Methyl bromide concentration can be then monitored using a thermal conductivity detector (Fumiscope®, from Key Chemical & Equipment, Clearwater, Fla.) throughout the fumigation operation. If concentrations are found to fall below target amounts during the fumigation, additional methyl bromide is added. After the fumigation, the seal is removed and the structure aerated. It is apparent that the same techniques can also be used for decontaminations of vehicles, trains, boats, or airplanes.

It is known in the fumigation industry that once airborne methyl bromide concentrations are below 3 ppm, the treated building and its contents are safe for reoccupation and for all normal activities. Post fumigation methyl bromide concentration can be measured using gas detector tubes, such as Kitagawa gas detector tubes manufactured by Matheson Safety Products, East Rutherford, N.J., or a Miran® infrared gas-detecting device from Thermo Environmental Instruments, Franklin, Mass. Given that methyl bromide is already registered by the EPA as a structural and commodity fumigant, it has long been determined that human contact with any of the particular contents of the building would pose no greater risk than contact with structural parts or surfaces of the building itself. Methyl bromide can be released effectively from the structure by aeration after the structure is unsealed. Further, current instrumentation already exists for field monitoring and clearing of methyl bromide without requirement for the use, as in the case of the prior art method of chlorine dioxide decontamination, of a one million dollar piece of equipment known as a Trace Atmospheric Gas Analyzer.

Bacteria test strips used as a means to confirm the disabling of germination of the pathogenic microbes are placed in multiple locations throughout the structure inclusive of desks and office articles as well as actual structural surfaces of the building itself. Therefore, the present inventive method differs from that of historical fumigation in its use in connection with microbes and the requirement for the use of strips of test bacteria spores to verify the effectiveness of any given structural cleanup.

In a further embodiment, the method of decontamination can be utilized for decontaminating articles contaminated by pathogenic microorganisms. A practical example of contaminated articles is packages of mails handled daily in the post offices. The process can be easier for the articles than for large structures because of their smaller sizes. The method comprises the steps of placing a contaminated article in a closed chamber, and sealing the chamber; introducing a methyl bromide gas into the sealed chamber to a concentration of methyl bromide sufficient to deactivate the pathogenic microorganisms and disable germination of the pathogenic bacteria spores, and maintaining the concentration of methyl bromide in the sealed chamber at a sufficient temperature for a sufficient period of time, and resulting in deactivating the pathogenic microorganisms and disabling germination of the pathogenic bacteria spores associated with the contaminated article. After the decontamination, the chamber is unsealed, and the methyl bromide gas is released. The treated article can be retrieved from the chamber for reuse when the methyl bromide concentration is below 3 ppm.

As stated previously, *B. subtilis* spore test strips are a universally accepted standard for determination of whether a bacterial spore has been deactivated by a treating agent or a treatment method. Therefore, based on the effectiveness demonstrated above, it is believed that the method of the present invention has broad applications against microorganisms, particularly Bacillus spores. More specifically, the method of the present invention can be utilized to decontaminate structures, or articles contaminated by pathogenic bacteria and their spores including, but not limited to, *Bacillus anthracis*, and its spores, *B. subtilis* var *niger* and its spores, and *B. stearothermophilus* and its spores.

In light of terrorism actions of September 2001, it is apparent that the method of the present invention has a very important value in terms of protecting public safety by effectively controlling further contaminations, which can be potentially spread from contaminated structures, and/or articles. It also has important economic values because of recovering those contaminated structures, or important articles.

EXAMPLE 1

Spore Strips

The University of Florida Sterilization Monitoring and Consulting Service, Dept. of Oral & Maxillofacial Surgery, Gainesville, Fla., provided combined species spores strips that contained $10^6$ spores of *B. subtilis* var. *niger* strips derived from ATCC #9372, and $10^5$ spores of *B. stearother-*

*mophilus* derived from ATCC #7953. The spore strips were in Schleicher & Schuell filter paper (#470, 6.4×38.1 mm) packaged in a Glassine® paper pouch. Glassine paper is permeable to sterilant but resistant to moisture and air at ambient temperature/pressure. These strips are standard indicators for verifying the efficacy of chemical, dry-heat, and steam sterilization equipment. After the methyl bromide exposures, the strips were incubated in tryptic soy broth as recommended by the strip manufacturer. At 48 hours, color change of the broth from purple to yellow indicates spore germination and vegetative growth of the Bacillus. If broth color does not change, the spores are not viable. Germination results reported here are based on a one-week incubation at temperatures of 55° C. for *B. stearothermophilus* and 35° C. for *B. subtilis* var. *niger*. The incubations were performed by University of Florida for the $10^6$ spores of *B. subtilis* var. *niger* strips and $10^5$ spores of *B. stearothermophilus* strips.

Methyl Bromide Exposures

Seven 9-liter glass desiccators were used as fumigation chambers (FIG. 1). Each chamber was equipped with a septum port in the lid and a 12-cm propeller attached to magnetic stir disk inside the base. Each fumigation trial consisted of simultaneously exposing spore strips to seven methyl bromide exposure conditions. Two spore strips were placed in each chamber before chambers were sealed with silicone vacuum grease. The chamber was placed on a magnetic stirring plate that spun the internal propeller at about 10 rps. Neat methyl bromide gas was withdrawn from the headspace of a partially filled 150-ml Whitey (Highland Heights, Ohio) stainless steel sample cylinder filled from a commercial cylinder of Meth-O-Gas (>99.5% methyl bromide, Great Lakes Chemical Company, West Lafayette, Ind., Anon. 1989). The sample cylinder was fitted with a Whitey DK series shut-off valve connected to a Kel-F syringe adapter with septum (Alltech Associates, Deerfield, Ill.). Headspace contaminants were purged by opening the valve and loosening and reseating the septum under a fume hood. Methyl bromide was then withdrawn through the septum with a gas syringe. The pressurized methyl bromide gas in the syringe was allowed to reach equilibrium with atmospheric pressure by escaping from the needle after septum withdrawal and before the dense gas (3.874 mg/ml) was injected into chambers. After each addition of 250 ml of methyl bromide gas, the chamber was relieved of pressure by inserting a syringe needle into the injection septum. After reaching temperature equilibrium, each chamber was again purged to equilibrate chamber pressure with atmospheric pressure. It was estimated that this pressure release resulted in a loss of no more than 8% of the introduced methyl bromide. A previous study (Scheffrahn & Su, Comparative Toxicity Of Methyl Bromide Against Ten Nearctic Termite Species (Isoptera: Termopsidae, Kalotermitidae, Rhinotermitidae). *J. Econ. Entomol.* 85:845–847, 1992) also showed methyl bromide loss by sorption of 6%. Chambers were held at 19° C. (room temperature) for 48 to 164 hours. Relative humidity inside the chambers was about 40%.

The test results expressed as germination of Bacillus sp. spores after exposure to methyl bromide in 9-liter glass chambers under selected concentration, temperature, and time conditions are shown in Table 1.

As shown at 19° C., *Bacillus stearothermophilus* spores were prevented from germinating at relatively low concentration of methyl bromide of 80 mg/l. However, *B. subtilis* spores were much more resistant. At an incubation temperature of 19° C., with a concentration of methyl bromide as high as 320 mg/l (theoretical value) and exposure time as long as 164 hours, *B. subtilis* spores were still able to germinate.

TABLE 1

| Temp ($°$ C.[1]) | MeBr Conc. (mg/l[2]) | Time (hours) | Dosage. (mg-hr/l) | Spore Germination | |
|---|---|---|---|---|---|
| | | | | B. stearo. | B. subtilis |
| 19 | 48 | 63 | 3,000 | yes | yes |
| 19 | 48 | 104 | 5,000 | yes | yes |
| 19 | 48 | 146 | 7,000 | yes | yes |
| 19 | 80 | 112 | 9,000 | no | yes |
| 19 | 80 | 134 | 11,000 | no | yes |
| 19 | 80 | 164 | 13,120 | no | yes |
| 19 | 160 | 164 | 26,240 | no | yes |

[1]Mean ± 0.4° C.
[2]Theoretical concentration based on methyl bromide volume introduced. Actual concentration is lower.

EXAMPLE 2

The same materials and experiment conditions of Example 1 were used in the Example 2, except the incubation temperatures and the concentrations of methyl bromide in the chambers. The incubation temperatures were raised up to 27° C. Methyl bromide concentration was raised up to 320 mg/l (theoretical value). Furthermore, because *B. sterothermophilus* spores showed to be more susceptible to methyl bromide than those of *B. subtilis* under the experimental conditions of Example 1, both strips in each chamber were incubated for *B. subtilis* in the experiment of Example 2.

In addition to spore strips, one chamber (320 mg/l methyl bromide, 27° C., 96 hrs) was fitted with a videotape, CD with data, ZIP diskette with data, calculator, AA battery, laser-printed document, disposable camera with partially exposed film, galvanized and stainless steel washers, and photographs (laser-jet and photo emulsion paper). Office commodity exposures were used to access the effect of methyl bromide on these office commodities commonly present in office buildings.

The test results expressed as germination of Bacillus sp. spores after exposure to methyl bromide in 9-liter glass chambers under selected concentration, temperature, and time conditions are shown in Table 2.

TABLE 2

| Temp ($°$ C.[1]) | MeBr Conc. (mg/l[2]) | Time (hours) | Dosage. (mg-hr/l) | Spore Germination | |
|---|---|---|---|---|---|
| | | | | B. stearo. | B. subtilis |
| 20 | 240 | 48 | 11,520 | nt[3] | yes |
| 20 | 320 | 72 | 23,040 | nt | yes |
| 20 | 320 | 96 | 30,720 | nt | yes |
| 27 | 240 | 48 | 11,520 | nt | yes |
| 27 | 320 | 72 | 23,040 | nt | no |
| 27 | 320 | 96 | 30,720 | nt | no |
| 27 | 320 | 96 | 30,720 | nt | no[4] |

[1]Mean ± 0.4° C.
[2]Theoretical concentration based on methyl bromide volume introduced. Actual concentration is lower.
[3]nt = not tested. In these tests, both strips were tested for *B. subtilis* germination.
[4]Chamber contained office commodities listed above.

As shown, when the exposure temperature was raised to 27° C. and with a methyl bromide concentration of 320 mg/l *B. subtilis* spore germination was successfully disabled, after exposure under such a condition for 72 hours.

Furthermore, at 320 mg/l for 96 hours, no observable damage had occurred to the office commodities even though spore viability was inhibited. Unaltered data were recovered from the storage media (video tape, CD, and Zip diskette), the calculator functioned, and the unexposed film was exposed and developed without damage.

EXAMPLE 3

The same materials and experiment conditions of Example 2 were used in the Example 3, except that the incubation temperature was further elevated to 32° C.

The test results expressed as germination of Bacillus sp. spores after exposure to methyl bromide in 9-liter glass chambers under selected concentration, temperature, and time conditions are shown in Table 3.

As shown, when the exposure temperature was further raised to 32° C., with a methyl bromide concentration of 240 mg/l *B. subtilis* spore germination was successfully disabled, after exposure under such a condition for only 38 hours, which was almost only half of the time period required at 27° C. This experiment further illustrated the importance of temperature in inhibiting germination of *B. subtilis* spores.

TABLE 3

| Temp ($°$ C.[1]) | MeBr Conc. (mg/l[2]) | Time (hours) | Dosage. (mg-hr/l) | Spore Germination B. stearo. | Spore Germination B. subtilis |
|---|---|---|---|---|---|
| 27 | 320 | 48 | 15,360 | nt[3] | no |
| 27 | 320 | 62 | 19,776 | nt | no |
| 32 | 160 | 72 | 11,520 | nt | yes |
| 32 | 240 | 48 | 11,520 | nt | no |
| 32 | 240 | 72 | 17,280 | nt | no |
| 32 | 320 | 38 | 12,160 | nt | no |
| 32 | 320 | 47 | 15,104 | nt | no |

[1]Mean ± 0.4° C.
[2]Theoretical concentration based on methyl bromide volume introduced. Actual concentration is lower.
[3]nt = not tested. In these tests, both strips were tested for *B. subtilis* germination.

It is noted, however, at 32° C. a methyl bromide concentration of 160 mg/l with an exposure time of 72 hours is not sufficient to prevent germination of the *B. subtilis* spores. This suggests that the dosage (concentration and time product) is not predictive of efficacy. Exposure temperature and methyl bromide concentration are more important in preventing spore germination than exposure time.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

EXAMPLE 4

Materials and Methods

Site Preparation. A partially furnished 10,000 ft$^3$ mobile home situated on a 100-acre State research facility was prepared for methyl bromide (MB) fumigation. The trailer was covered with 2 vinyl-coated nylon tarpaulins that were clamped together and sealed at ground level with sand "snakes". The trailer contained elements of both residential and office environments. The floor was carpeted, the walls were paneled with wood, and the ceiling was "popcorned". Furnishings included a desk with drawers, a bed, a plush reclining chair, cabinets, closets, and light fixtures. Office furnishings included a Dell 133 MHz 586 personal computer (PC), electronic balance, videotape, CD with data, ZIP diskette with data, hand calculator, "D" battery, laser-printed document, disposable camera with partially exposed film, 35 mm film slides, galvanized and stainless steel washers, copper-clad zinc pennies, chrome and steel clamp, photographs (color ink-jet and photo emulsion paper), newsprint, slick newsprint, magazines, and a black and white LaserJet document.

Monitoring lines were placed in the kitchen and bathroom to measure MB concentration during the fumigation. The terminus of a "shooting" hose from which the MB was introduced was clamped inside a weighted bucket. One fan was placed in front of the "shooting" bucket and a second was placed in the hallway. Wireless temperature and humidity sensors (wireless weather station WS 2010, La Crosse, Technology Ltd., La Crescent, Minn.) were placed at the kitchen ceiling, the kitchen floor, and the second bedroom closet. Temperature data loggers (Watch Dog 225 and 450, Spectrum technologies, Inc., Plainfield, Ill.) were placed on the arm of the reclining chair, the PC desk, the second bedroom window air-conditioner, and the bathroom countertop. Oil-filled radiant heaters (Delonghi,1650 W) were placed in the living room, kitchen, first bedroom, hallway, bathroom entry, and second bedroom.

Spore Strips. Combined-species spore strips (Raven Biological Laboratories, Omaha, Nebr.) with 10$^6$ spores of *B. subtilis* var. *niger* ATCC # 9372 and 10$^5$ of *B. stearothermophilus* ATCC #7953 were provided by the University of Florida Sterilization Monitoring and Consulting Service, Dept. of Oral & Maxillofacial Surgery, Gainesville, Fla. Additionally, *B. subtilis* var. *niger* strips containing 10$^8$ spores were obtained directly from Raven Biological Laboratories. Spore strips were in Schleicher & Schuell filter paper (#470, 6.4×38.1 mm) packaged in Glassine® paper pouches. Glassine paper is permeable to a fumigant but resistant to moisture and penetration by external microbes. These strips are standard indicators for verifying the efficacy of both chemical (ethylene oxide), dry-heat, and steam sterilization equipment. These strips were also used to verify the sporicidal efficacy of chlorine dioxide in the 30,000 ft$^3$ Daschle Suite of the Hart Senate Building. After the methyl bromide fumigation, the strips were incubated in tryptic soy broth as recommended by the strip manufacturer. At 48 hours, color change of the broth from purple to yellow indicates spore germination and vegetative growth of the Bacillus. If broth color does not change after 1 week, the spores are not viable and no germination has occurred. Germination results (pass=no growth, fail=growth) reported herein (Table 4) are based on 1-week incubations at temperatures of 55° C. for *B. stearothermophilus* and 35° C. for *B. subtilis*.

Twenty sites within the trailer were selected that represented expected and worst-case spore contamination sites (Table 4). At each site, two combined-species strips and two 10$^8$ *B. subtilis* strips were positioned either by gravity or clear tape for a total placement of 80 spore strips. A total of 40 additional control strips were stored at room temperature in the laboratory. After MB fumigation, all strips were recovered from placement sites and returned, along with unfumigated control strips, to Gainesville and Omaha for incubation.

Fumigation and Aeration. Concentration, temperature, and time targets of 320 oz/1,000 ft$^3$, 95° F., and 48 hours, respectively, were selected based on conditions toxic to *Bacillus subtilis* spores. From 9:11–10:34 on 21 Feb. 2002, 204.4 lbs of MB was introduced inside the trailer. Throughout the fumigation and aeration procedures, indoor concentration of MB was measured from monitoring lines in the kitchen and bathroom using a Fumiscope® thermal conductivity detector (Key Chemical and Equipment Co., Clearwater, Fla.) with an accuracy of 2 percent full scale. At 48 hours post-equilibrium, a ca. 12 by 4 inch elliptical vent was opened in a west-facing seam to begin the aeration process. MB measurements in the kitchen were taken hourly for the first 8 hours during which time the aeration vent was enlarged to 18 by 4 inches at 2 hours into aeration, and ultimately, 36 by 10 inches at 6 hours into aeration. At 24 hours into aeration, a fan was placed into the aeration vent and a second aeration vent was opened in the south seam. At 25 hours after aeration was initiated, both tarpaulins were removed from the trailer to complete the residual aeration process.

Airborne MB Residues. During fumigation and aeration, MB residues were monitored periodically at five locations: downwind at 20, 100, and 150 feet from the trailer, at College Avenue 140 ft due east of the trailer, and at the Florida Dept. of Forestry Fire facility 140 ft. southeast of the trailer. MB residues were measured using Kitagawa #157SB gas detector tubes (0.4–80 ppm; Matheson Inc., East Rutherford, N.J.) and a pump assembly. Measurements were taken 3 ft above ground and directly downwind from the trailer or aeration vent while wearing a self-contained breathing apparatus.

Results and Discussion

Fumigation and Aeration. An equilibrium concentration of 335 oz/1,000 ft$^3$ (335 mg/l) was attained at 11:40 on February 21. As shown in FIG. 1, after the initial application of 204.4 lbs, three additional applications of 35.4, 35.4, and 31.3 lbs of MB were made on 21 February 19:00, 22 February 7:15, and 22 February 18:00, respectively, to supplement diffusive and sorptive losses for a total introduction of 306.5 lbs. These cumulative applications resulted in corresponding peaks in MB concentration and yielded a time-weighted mean concentration of 303.7 oz/1000 ft$^3$ during the 48-hour fumigation for an accumulated dosage of 14,578 oz-hr/10,000 ft$^3$ (mg-hr/l). To maintain a trailer temperature near 95° F., between 0–6 heaters were turned on as required to adjust for ambient temperature changes and radiant daytime heating as indicated by the wireless sensors. Temperatures reported in Table 4 were recorded by the four temperature loggers placed in proximity of the spore strips. Mean relative humidity during the fumigation, recorded using the bathroom logger with RH capability, was 62% (min. 50%, max. 69%). During the fumigation, wireless sensors displayed the following max./min. temperature and % humidity values at three locations: kitchen ceiling (T1, 100.4/90.5° F., 58/42%), kitchen floor (T2, 98.7/90.5° F., 59/42%), and second bedroom closet (T3, 100.7/92.1° F., 60/39%).

Aeration was initiated at 12:15 on February 23 when MB concentration in the kitchen was 274 oz/1,000 ft$^3$. Concentration steadily declined at a rate of ca. 29 oz/1,000 ft$^3$ per hour to 43 oz/1,000 ft$^3$ at 20:15. At 8:15 on 24 February, MB concentration was 4 oz/1,000 ft$^3$ and at 24-hours after initiation of aeration, MB was not detected by the Fumiscope.

During the fumigation, a single detector tube reading of 2.5 ppm was measured 20 ft downwind of the trailer (Table 5). All other pre-aeration readings were between 0–1 ppm. As expected, aeration readings were higher with the downwind readings at 20 feet measured at 5, 7.5, 45, 45, and 60 ppm. All readings were greatly influenced by erratic wind movements; however, readings at 100 ft and beyond did not exceed 3 ppm at any location.

Efficacy. Spore strips were recovered from the trailer sites after tarp removal and MB aeration below 3 ppm on February 24 at 14:00. Four strips were collected from each site and two of each type were placed in envelopes that also contained a single control (unfumigated) strip stored in the laboratory. Fumigated and unfumigated strips were incubation in Gainesville on February 25 and in Omaha on 26 February 02. In Gainesville, one strip from each site was incubated for *B. subtilis* germination, the second strip for *B. stearothermophilus*.

Table 4 lists results of spore strip incubations. Spores on all of the 10$^6$ *B. subtilis* and all of the 10$^5$ *B. stearothermophilus* strips were killed by the MB fumigation indicating that conditions lethal to the bacterial spores were encountered at each of the 20 trailer sites tested. Each site also yielded at least one *B. subtilis* 10$^8$ strip that was not viable after fumigation. Both *B. subtilis* 10$^8$ strips produced no vegetative cells during incubation at 16 sites. Only one 10$^8$ strip each survived in four other sites. Therefore, at 90% (16) of the sites, all four test strips were killed, while at 10% of the sites 3 of 4 strips were killed.

Collateral Damage. Equipment and materials were not damaged or otherwise visually or functionally affected by exposure to MB during the trailer fumigation. The computer continued to run and process data normally, the undeveloped film was exposed and developed and prints appeared normal. The electronic balance functioned normally, and printed materials remained as before the MB exposure. After aeration, however, a lingering odor was detected inside the trailer for up to 7 days after the fumigation. The odor could be described as "tinny" or organic—reminiscent of corn tortillas.

Comparison of MB with Chorine Dioxide. As of this writing, there are no USEPA approved whole-structure remediation methods for Bacillus spore decontamination of whole, large, furnished buildings. Although chlorine dioxide, in addition to other methods, was used to remediate the Daschle Suite, it is not practical for use as a whole-structure decontaminant because of collateral damage, inability to reach equilibrium, and inability to produce large quantities. MB, however, has been a proven and efficacious whole-structure fumigant for more than 50 years. Chlorine dioxide is also expensive, highly explosive, highly corrosive, and difficult to store.

Conclusions

This study demonstrates that Bacillus spores can be controlled with MB under whole-structure conditions without any collateral damage. Minor modifications to existing MB fumigation methods include mean exposure temperatures of at least 90° F. and concentrations approximating 300 oz/1,000 ft$^3$ for 48 hours.

TABLE 4

Spore strip location, proximal ambient temperature conditions, and incubation results (pass = no spore germination occurred; fail = spore germination occurred) for 80 strips at 303.7 oz/1,000 ft$^3$ methyl bromide exposure for 48 hours in trailer.

| | Exposure Temp. ° F. | | | 10$^6$ | 10$^5$ | *B. subtilis* 10$^8$ | |
| --- | --- | --- | --- | --- | --- | --- | --- |
| Trailer Loc. & Descr. | Mean | Max. | Min. | *B. sub.* | *B. stear.* | Strip A | Strip B |
| 1-Floor vent, inside ducting | 95.12 | 98.8 | 89.6 | pass | pass | pass | fail |
| 2-Under carpet fabric | 95.12 | 98.8 | 89.6 | pass | pass | pass | pass |

TABLE 4-continued

Spore strip location, proximal ambient temperature conditions, and incubation results (pass = no spore germination occurred; fail = spore germination occurred) for 80 strips at 303.7 oz/1,000 ft³ methyl bromide exposure for 48 hours in trailer.

| Trailer Loc. & Descr. | Exposure Temp. °F. Mean | Max. | Min. | $10^6$ B. sub. | $10^5$ B. stear. | B. subtilis $10^8$ Strip A | Strip B |
|---|---|---|---|---|---|---|---|
| 3-Behind wall paneling in insulation | 95.12 | 98.8 | 89.6 | pass | pass | pass | pass |
| 4-Wall plug outlet, covered | 95.12 | 98.8 | 89.6 | pass | pass | pass | pass |
| 5-Wall surface, in closed folder | 95.12 | 98.8 | 89.6 | pass | pass | pass | pass |
| 6-Closed kitchen cabinet | 95.07 | 98.8 | 89.6 | pass | pass | pass | pass |
| 7-PC keyboard, inside back cover | 95.07 | 98.8 | 89.6 | pass | pass | pass | pass |
| 8-PC CD tray, closed | 95.07 | 98.8 | 89.6 | pass | pass | pass | pass |
| 9-Desk drawer, closed | 95.07 | 98.8 | 89.6 | pass | pass | pass | pass |
| 10-Desk drawer, in closed hanging file | 95.07 | 98.8 | 89.6 | pass | pass | pass | pass |
| 11-Ceiling surface, exposed | 95.07 | 98.8 | 89.6 | pass | pass | pass | pass |
| 12-Floor surface, in closed folder | 95.07 | 98.8 | 89.6 | pass | pass | pass | fail |
| 13-Mattress, under box spring | 95.07 | 98.8 | 89.6 | pass | pass | fail | pass |
| 14-Hall closet, closed | 90.29 | 94.1 | 83.6 | pass | pass | fail | pass |
| 15-Medicine cabinet, closed | 90.29 | 94.1 | 83.6 | pass | pass | pass | pass |
| 16-Light fixture, secured globe | 90.29 | 94.1 | 83.6 | pass | pass | pass | pass |
| 17-Central AC inlet, behind filter | 90.29 | 94.1 | 83.6 | pass | pass | pass | pass |
| 18-Window AC, behind filter | 93.24 | 100.2 | 88.2 | pass | pass | pass | pass |
| 19-Under newspapers | 93.24 | 100.2 | 88.2 | pass | pass | pass | pass |
| 20-Recliner chair, under cover fabric | 95.12 | 98.8 | 89.6 | pass | pass | pass | pass |

TABLE 5

Detector tube locations, wind conditions, and readings at various times during the trailer fumigation and aeration.

| Date | Fumigation Status | Time | Wind Direction | Wind Speed mph | Direction from trailer | Distance from trailer or vent | Tube reading ppm |
|---|---|---|---|---|---|---|---|
| 21-Feb | 4 hr into fumigation | 16:20 | SSE | 1–2 | NNW | 20 | 2.5 |
| 21-Feb | 4 hr into fumigation | 16:24 | SSE | 1–2 | NNW | 100 | 0.7 |
| 21-Feb | 4 hr into fumigation | 16:30 | SSE | 1–2 | NNW | 150 | trace |
| 21-Feb | 4 hr into fumigation | 16:35 | — | still | E | 140, street | 0.0 |
| 21-Feb | 4 hr into fumigation | 16:39 | — | still | SE | 140, fire lab | 0.0 |
| 22-Feb | 18 hr into fumigation | 6:38 | — | still | N | 20 | 1.0 |
| 22-Feb | 18 hr into fumigation | 6:45 | — | still | N | 100 | 0.0 |
| 22-Feb | 18 hr into fumigation | 6:54 | — | still | E | 140, street | 0.0 |
| 22-Feb | 18 hr into fumigation | 6:58 | — | still | SE | 140, fire lab | 0.0 |
| 22-Feb | 30 hr into fumigation | 17:26 | S | 5–10 | N | 20 | 1.0 |
| 22-Feb | 30 hr into fumigation | 17:34 | S | 5–10 | N | 100 | 0.0 |
| 22-Feb | 30 hr into fumigation | 17:40 | S | 5–10 | E | 140, street | 0.0 |
| 22-Feb | 30 hr into fumigation | 17:44 | S | 5–10 | SE | 140, fire lab | 0.0 |
| 23-Feb | begin aeration | 12:23 | S | 5–12 | N | 20 | 5.0 |
| 23-Feb | begin aeration | 12:35 | S | 5–12 | N | 100 | 1.2 |
| 23-Feb | begin aeration | 12:42 | S | 5–12 | N | 150 | 1.2 |
| 23-Feb | begin aeration | 12:45 | S | 5–12 | E | 140, street | 0.0 |
| 23-Feb | begin aeration | 12:50 | S | 5–12 | SE | 140, fire lab | 0.0 |
| 23-Feb | 1 hr into aeration | 13:18 | SSW | 10–20 | NNE | 20 | 7.5 |
| 23-Feb | 1 hr into aeration | 13:25 | SSW | 10–20 | NNE | 100 | 3.0 |
| 23-Feb | 1 hr into aeration | 13:35 | SSW | 10–20 | NNE | 150 | trace |
| 23-Feb | 1 hr into aeration | 13:40 | SSW | 5–15 | E | 140, street | 0.0 |

TABLE 5-continued

Detector tube locations, wind conditions, and readings at various times during the trailer fumigation and aeration.

| Date | Fumigation Status | Time | Wind Direction | Wind Speed mph | Direction from trailer | Distance from trailer or vent | Tube reading ppm |
|---|---|---|---|---|---|---|---|
| 23-Feb | 1 hr into aeration | 13:45 | SSW | 5–15 | SE | 140, fire lab | 0.0 |
| 23-Feb | 2 hr into aeration | 14:18 | var. SW | 15–20 | NE | 20 | 45.0 |
| 23-Feb | 2 hr into aeration | 14:25 | var. SW | 15–20 | NE | 100 | 1.5 |
| 23-Feb | 2 hr into aeration | 14:34 | var. SW | 15–20 | NE | 150 | 1.0 |
| 23-Feb | 2 hr into aeration | 14:38 | WSW | 10–20 | E | 140, street | 0.0 |
| 23-Feb | 2 hr into aeration | 14:45 | WSW | 10–20 | SE | 140, fire lab | 0.0 |
| 23-Feb | 4 hr into aeration | 16:10 | var. | 0–3 | N | 20 | 45.0 |
| 23-Feb | 4 hr into aeration | 16:18 | SSW | 0–3 | N | 100 | 1.0 |
| 23-Feb | 4 hr into aeration | 16:22 | var. | 0–5 | NE | 150 | 0.0 |
| 23-Feb | 4 hr into aeration | 16:30 | W | 0–5 | E | 140, street | 0.0 |
| 23-Feb | 4 hr into aeration | 16:34 | WSW | 0–5 | SE | 140, fire lab | 0.0 |
| 23-Feb | 8 hr into aeration | 20:15 | N | 5–20 | SE | 20 | 60.0 |
| 23-Feb | 8 hr into aeration | 20:24 | N | 5–20 | E | 100 | 0.0 |
| 23-Feb | 8 hr into aeration | 20:28 | N | 5–20 | SE | 150 | 0.0 |
| 23-Feb | 8 hr into aeration | 20:35 | N | 5–20 | E | 140, street | 0.0 |
| 23-Feb | 8 hr into aeration | 20:40 | N | 5–20 | SE | 140, fire lab | 0.0 |

We claim:

1. A method of decontaminating a structure contaminated by pathogenic microorganisms comprising the steps of:
   (a) sealing a contaminated structure sufficiently to enable retention of a gas,
   (b) introducing methyl bromide gas into sealed contaminated structure to a concentration of methyl bromide in an amount sufficient to deactivate said pathogenic microorganisms and disable germination of pathogenic bacteria spores, and
   (c) maintaining said sealed contaminated structure with said concentration of methyl bromide at a sufficient temperature for a sufficient period of time, and resulting in deactivating said pathogenic microorganisms and disabling germination of said pathogenic bacteria spores associated with said contaminated structure.

2. The method of decontaminating a structure of claim 1 further comprising the step of unsealing and aerating decontaminated structure to release said methyl bromide gas for reuse of said structure.

3. The method of decontaminating a structure of claim 1, wherein said pathogenic bacteria and spores of said pathogenic bacteria comprise bacillus anthracis and its spores, B. subtilis var niger and its spores, and B. stearothermophilus and its spores.

4. The method of decontaminating a structure of claim 1, wherein said structure comprises a room, a residential or commercial building, a mobile home, a vehicle, a train, a boat, and an airplane.

5. The method of decontaminating a structure of claim 1, wherein said sufficient temperature is greater than 20° C.

6. The method of decontaminating a structure of claim 5, wherein said sufficient temperature is greater than 25° C.

7. The method of decontaminating a structure of claim 5, wherein said sufficient temperature is approximately between 25° C. and 40° C.

8. The method of decontaminating a structure of claim 6, wherein said concentration of methyl bromide is about 200 mg/l and above.

9. The method of decontaminating a structure of claim 1, wherein said concentration of methyl bromide is about 250 mg/l and above.

10. The method of decontaminating a structure of claim 1, wherein said concentration is a mean concentration of approximately 303 mg/l during the decontamination.

11. The method of decontaminating a structure of claim 8, wherein said sufficient time is greater than 30 hours.

12. The method of decontaminating a structure of claim 9, wherein said sufficient time is approximately 48 hours.

13. The method of decontaminating a structure of claim 1 further comprising introducing an additive into said sealed contaminated structure.

14. The method of decontaminating a structure of claim 13, wherein said additive is chloropicrin.

15. A method of decontaminating an article contaminated by pathogenic microorganisms comprising the steps of:
   (a) placing said contaminated article in a closed chamber, and sealing said chamber,
   (b) introducing methyl bromide gas into sealed chamber to a concentration of methyl bromide sufficient to deactivate said pathogenic microorganisms and disabling germination of said pathogenic bacteria spores, and
   (c) maintaining said concentration of methyl bromide in said sealed chamber at a sufficient temperature for a sufficient period of time, and resulting in deactivating said pathogenic microorganisms and disabling germination of said pathogenic bacteria spores associated with said contaminated article.

16. The method of decontaminating an article of claim 15 further comprising the step of releasing said methyl bromide gas from said chamber for reuse of said article.

17. The method of decontaminating an article of claim 15, wherein said pathogenic microorganisms and pathogenic bacteria spores comprise bacillus anthracis and its spores, B. subtilis var niger and its spores, and B. stearothermophilus and its spores.

18. The method of decontaminating an article of claim 15, wherein said sufficient temperature is greater than 20° C.

19. The method of decontaminating an article of claim 18, wherein said sufficient temperature is greater than 25° C.

20. The method of decontaminating an article of claim 15, wherein said sufficient temperature is approximately between 25° C. and 40° C.

21. The method of decontaminating an article of claim 19, wherein said concentration of methyl bromide is about 200 mg/l and above.

22. The method of decontaminating an article of claim 21, wherein said concentration of methyl bromide is about 250 mg/l and above.

23. The method of decontaminating an article of claim 15, wherein said concentration is a mean concentration of approximately 303 mg/l during the decontamination.

24. The method of decontaminating an article of claim 21, wherein said sufficient time is greater than 30 hours.

25. The method of decontaminating an article of claim 23, wherein said sufficient time is approximately 48 hours.

26. A method of decontaminating a structure contaminated by pathogenic microorganisms comprising the steps of:

(a) sealing a contaminated structure sufficiently to enable retention of a gas, (b) introducing methyl bromide gas into sealed contaminated structure to achieve a concentration of methyl bromide about 200 mg/l and above, and (c) maintaining said sealed contaminated structure with said concentration of methyl bromide at a temperature greater than 25° C. for a sufficient period of time, and resulting in deactivating said pathogenic microorganisms and disabling germination of said pathogenic bacteria spores associated with said contaminated structure.

27. The method of decontaminating a structure of claim 26, wherein said sufficient time is greater than 30 hours.

* * * * *